United States Patent [19]
Baldwin et al.

[11] Patent Number: 6,042,827
[45] Date of Patent: Mar. 28, 2000

[54] ANTI-IDIOTYPIC ANTIBODY INDUCTION OF ANTI-TUMOR RESPONSE

[75] Inventors: Robert William Baldwin; Linda Gillian Durrant; Eric Bertram Austin, all of Nottingham, United Kingdom; Vera S. Byers, San Francisco, Calif.

[73] Assignee: Cancer Research Campaign Technology Limited, London, United Kingdom

[21] Appl. No.: 08/278,693

[22] Filed: Jul. 21, 1994

Related U.S. Application Data

[63] Continuation of application No. 08/116,310, Sep. 3, 1993, abandoned, which is a continuation of application No. 07/799,849, Nov. 27, 1991, abandoned, which is a continuation of application No. 07/258,911, Oct. 17, 1988, abandoned.

[51] Int. Cl.[7] ........................ A61K 39/395; C07K 16/42; C12N 5/20
[52] U.S. Cl. ..................... 424/131.1; 424/133.1; 424/135.1; 424/184.1; 435/327; 435/328; 530/387.2; 530/387.3; 530/387.1; 530/809
[58] Field of Search ............... 424/131.1, 184.1, 424/138.1, 135.1, 155.1, 156.1, 174.1, 133.1, 134.1; 435/172.2, 240.27, 70.21, 327, 328; 530/387.2, 387.1, 387.7, 388.8, 389.7, 809; 935/89, 100, 107

[56] References Cited

U.S. PATENT DOCUMENTS

| | | | |
|---|---|---|---|
| 4,699,880 | 10/1987 | Goldstein | 435/70.21 |
| 4,708,862 | 11/1987 | Baldwin | 424/1.49 |
| 4,918,164 | 4/1990 | Hellstrom et al. | 530/387.2 |

OTHER PUBLICATIONS

Baldwin et al., Summary Report, "Cancer Research Technology".
Roitt, Immunology, Mosby and Company, pp. 25.9–25.10, 1993.
Denton, et al., Int. J. Cancer, vol. 57:10–14, 1994.
Robins, R.A., et al., "Antitumor Immune Response and Interleukin 2 Production Induced in Colorectal Cancer Patients by Immunization With Human Monoclonal Anti–Idiotypic Antibody," *Cancer Research*51, pp. 5425–5429 (Oct. 1, 1991).
Girardet, C., "Immunochemical Characterization of Two Antigens Recognized by New Monoclonal Antibodies Against Human Colon Carcinoma," *The Journal of Immunology*136:4, pp. 1497–1503 (Feb. 15, 1986).
Embleton, M.J., "Antitumour Reactions of Monoclonal Antibody Against a Human Osteogenic–Sarcoma Cell Line," *Br. J. Cancer*43, pp. 582–587 (1981).
DeFreitas et al., Current Topics in Microbiology and Immunology 119: 75–89, 1985.
Rowe et al., IRCS Med. Sci. 13: pp. 936–937, 1985.
Herlyn et al., Hybridoma 5 (Suppl.1): S51–S58, 1986.
Strelkauskas, Human Huybridomas, Marcel Dekker, New York, 1987, pp. 1–22.
Heyman et al. (1992) J. Exp. Med. 155:994.
Forstrom et al. (1983) Nature 303:627.
Lee et al. (1985) Proc. Natl. Acad. Sci. USA 82:6286.
Herlyn et al. (1987) Eur. J. Immunol. 17:1649.
Viale et al. (1987) J. Immunol. 139:4250.
Kennedy et al. (1985) J. Exp. Med 161:1432.
Raychaudhuri et al. (1987) J. Immunol. 139:271.
Raychaudhuri et al. (1987) J. Immunol. 139:3902.
Pimm et al. (1985) J. Nucl. Med. 26:1011.
Robins et al. (1986) J. Immunol. Meths. 90:165.

*Primary Examiner*—Ronald B. Schwadron
*Attorney, Agent, or Firm*—Townsend and Townsend and Crew LLP

[57] ABSTRACT

Novel compositions and methods are described for stimulating a patient's immune system to tumor cells which bear a gp72 tumor-associated antigen and thereby eliciting a tumoricidal effect. Anti-idiotypic human monoclonal antibodies and idiotopic regions thereof to primary antibodies which bind selectively to an antigenic determinant of gp72 are provided to mediate the humoral and cellular components of the patient's immune system. The immunogenic agents find use both in vivo and in vitro.

5 Claims, No Drawings

ANTI-IDIOTYPIC ANTIBODY INDUCTION OF ANTI-TUMOR RESPONSE

This application is a continuation of application Ser. No. 08/116,310, filed Sep. 3, 1993, now abandoned, in turn, a continuation of Ser, No. 07/799,849, filed Nov. 27, 1991, now abandoned, which is, in turn, a continuation of Ser. No. 07/258,911, Filed Oct. 17, 1988, now abandoned.

FIELD OF THE INVENTION

This invention relates generally to novel immunogenic compositions and methods for selectively treating cancer and, more particularly, to the production of human anti-idiotypic monoclonal antibodies which are capable of stimulating an antitumor response in an immunized patient.

BACKGROUND OF THE INVENTION

As a result of the introduction of hybridoma technology in the late 1970's, monoclonal antibodies, mostly of murine origin, have been made to many types of human cancer. Most of the tumor markers recognized by the xenogeneic monoclonal antibodies are not strictly tumor-specific, but are shared by tumors and certain normal and/or fetal tissues and are therefore referred to as tumor-associated antigens. Whether these tumor-associated antigens, identified by xenogeneic antibodies, are capable of evoking an antitumor response in cancer patients, and whether such antigens are even related to the immune response to autologous tumors in cancer patients, remains to be determined. It is widely felt that tumor growth and dissemination may be due to the lack of an immune response, either because tumor-associated antigens escape recognition or any antitumor responses are suppressed. Thus, antigens which can be made immunogenic might potentially be useful to induce antitumor immunity for therapeutic and possibly prophylactic benefits.

One approach toward manipulating the immune response to such tumor-associated antigens is based on idiotypic interactions. The unique antigenic determinants in and around the antigen combining site (paratope) of an immunoglobulin molecule are known as idiotopes, and the sum of all idiotopes present on the variable portion of a given antibody is referred to as its idiotype. Idiotypes are serologically defined, since injection of a primary antibody which binds an epitope of the antigen of interest may induce the production of anti-idiotypic antibodies.

When the binding between primary antibody and anti-idiotypic antibody is inhibited by the antigen to which the primary antibody is directed, the idiotype is considered to be binding-site related. In essence, the anti-idiotypic antibody recognizes a paratope-associated idiotope of the primary antibody. Since both the anti-idiotypic antibody and antigen bind to primary antibody, the anti-idiotypic antibody and antigen may share a similar three-dimensional conformation which represents the so-called "internal image" of the epitope. There may be reactions between primary antibody and other anti-idiotypic antibodies which are not inhibited by antigen, which may involve idiotopes of primary antibody which are spatially distinct from the paratope binding site, yet are still capable of regulating the immune response.

Anti-idiotypic antibodies which act as internal images of a tumor antigen may be used to prime a de novo response to the tumor antigen. By presenting these images of antigenic epitopes in a different molecular environment, responses may be activated which would otherwise be silent. Nisonoff and Lamoyi, *Clin. Immunol. Immunopathol.* (1981) 21:397. That is, when the anti-idiotype represents the conformational mirror-image of the antigen, it may substitute for nominal antigen and elicit a primary antibody-like response. Additionally, the anti-idiotypic antibody which mimics antigen may also select or amplify any pre-existing antitumor repertoire by the up regulation of a normally suppressed response. Most naturally-occurring anti-idiotypic populations contain few internal image anti-idiotypes, whereas xenogeneic anti-idiotypic antibodies more frequently succeed as internal image immunogens. Ibid.

Anti-idiotypic antibodies which do not bear the internal image of antigen may also induce antitumor responses by influencing the regulatory idiotypic network. See, Bona, 1984, in *Idiotypy in Biology and Medicine,* Kohler et al., eds., Academic Press, pp. 29–42. Thus antibodies to framework-associated idiotopes, or regulatory idiotopes, may select or amplify T and/or B cell clones with specificity for tumor antigens. Some evidence, however, suggests that this group of anti-idiotypic antibodies can prime a humoral response but are unable to cause maturation of B cells without further challenge with the nominal antigen (Heyman et al., *J. Exp. Med.* (1982) 155:994), and thus combination with an internal image anti-idiotypic antibody may be necessary to evoke a desired antitumor response.

Antitumor responses induced by anti-idiotypic manipulation have been shown against both murine (Forstrom et al., *Nature* (1983) 303:627; Lee et al., *Proc. Natl. Acad. Sci. USA* (1985) 82:6286) and human (Herlyn et al., *Eur. J. Immunol.* (1987) 17:1649; Viale et al., *J. Immunol.* (1987) 139:4250) tumor-associated antigens. Injection of xenogeneic anti-idiotypic antibody has reportedly induced antitumor responses leading to the suppression of tumor growth (Kennedy et al., *J. Exp. Med.* (1985) 161:1432; Raychaudhuri et al., *J. Immunol.* (1987) 139:271). However, recent evidence has shown that the presence of certain non-defined epitopes on both anti-idiotypic antibody and T-helper cells are important in the induction of tumor immunity, and different anti-idiotypes may have different effects on tumor growth (Raychaudhuri et al., *J. Immunol.* (1987) 139:3902).

A glycoprotein antigen of 72 kilodalton molecular weight (gp72) has been associated with colorectal, ovarian carcinomas, osteogenic sarcomas, and other malignancies (Price et al., *Brit. J. Cancer* (1984) 49:809; Campbell et al., *Int. J. Cancer* (1984) 34:31; Powell et al., *Amer. J. Obstet. Gynecol.* (1987) 157:28), as originally identified in the 791T sarcoma cell line. Murine monoclonal antibody 791T/36 reacts with a determinant of the gp72 antigen. Embleton et al., *Br. J. Cancer* (1981) 43:582. This monoclonal antibody has been coupled to imaging agents for use in the immunoscintigraphy of tumors, and has been coupled to cytotoxins such as ricin A chain, daunomycin and methotrexate and used as a targeting molecule. Patients receiving monoclonal antibody 791T/36 or ricin A chain-791T/36 immunoconjugates have been shown to develop anti-idiotypic antibodies. Rowe et al., *IRCS Medical Science* (1985) 13:936; Pimm et al., *J. Nucl. Med.* (1985) 26:1011; and Robins et al., *J. Immunol. Meths.* (1986) 90:165.

The use of anti-idiotypic antibodies to manipulate immune responses is a potentially new approach to cancer therapy. However, the vast majority of anti-idiotype polyclonal and monoclonal antibodies have been produced in animals other than man. These antibodies possess major disadvantages for treatment of tumors in humans. The continuous exposure of heterologous immunoglobulin molecules which may be required to induce an antitumor response may lead to the production of anti-isotypic antibodies and the rapid elimination of the anti-idiotype.

One possible way to overcome these difficulties is through the administration of human anti-idiotypic antibodies, preferably monoclonal. It is not at all clear, however, that the human tumor-associated antigens uncovered with xenogeneic antibodies are capable of evoking an antitumor response in humans. Moreover, the existence of human antibodies which are internal images of particular antigenic epitopes of the gp72 molecule is unknown. The surprising discovery of the human anti-idiotypic monoclonal antibodies of the present invention overcomes several of these problems and fulfills other related needs.

SUMMARY OF THE INVENTION

The present invention is concerned with the discovery of novel human monoclonal antibodies which are the anti-idiotype of primary antibodies which bind to the tumor-associated gp72 antigen. The gp72 antigen can be found on a variety of tumors, including colorectal carcinomas, ovarian carcinomas, and osteogenic sarcomas. In one embodiment the human anti-idiotypic antibodies of the invention are able to complex with the primary antibodies to gp72 and block the binding of said antibody to the antigen. The human anti-idiotype, illustrated herein by antibody 105AD7, may be an internal image of an epitope or other determinant of the gp72 antigen. By "internal image" is meant an antibody which possesses idiotopes which are conformationally similar or mimic an antigenic epitope.

In other embodiments the invention concerns methods and compositions useful in treating mammals with tumors which bear the gp72 antigen. An immunogenically or therapeutically effective amount of a human monoclonal antibody or idiotopic region thereof which is the anti-idiotype of a primary antibody which binds specifically to gp72 is employed in the composition and administered to the diseased host. The anti-idiotypic antibody is capable of eliciting a protective immune response in the host to the gp72 antigen, which response inhibits or kills tumor cells carrying the gp72 marker, thereby ameliorating or eliminating the disease caused by said antigen-bearing tumor cells. The immune response may take the form of humoral antibody response which activates serum complement and/or mediates antibody-dependent cellular cytotoxicity. The host response may also involve cell-mediated immunity, in the form of T helper cells, T suppressor cells, or cytotoxic T cells, for instance, which may directly or indirectly mediate the triggering or amplification of tumor antigen-specific suppression or rejection. To facilitate administration and effectiveness of the human anti-idiotypic composition, pharmaceutically-acceptable carriers and adjuvants may be included in the formulation.

DESCRIPTION OF THE SPECIFIC EMBODIMENTS

In accordance with the present invention, novel immortalized cells capable of producing human monoclonal antibodies and compositions comprising such antibodies are provided, wherein the human monoclonal antibodies are the anti-idiotypes of antibodies which bind selectively to the tumor-associated gp72 antigen. Administration of the anti-idiotypic antibody to a host containing tumor cells which bear gp72 antigen results in a protective immune response which inhibits or kills the tumor cells.

The anti-idiotypic human monoclonal antibodies of the invention may be prepared by immortalizing nucleic acid sequences that encode antibodies or idiotopic regions thereof specific for idiotopes of antibodies which bind selectively to gp72 antigenic determinants or epitopes thereof. The immortalization process may be carried out by hybridoma fusion techniques, by viral transformation of human antibody-producing lymphocytes, or by techniques that combine cell fusion and viral transformation methodologies.

According to one embodiment of the present invention, human monoclonal anti-idiotype antibodies are prepared using a combination of Epstein-Barr virus (EBV) transformation and hybridoma fusion techniques such as those described by Kozbor et al., Proc. Natl. Acad. Sci. (1982) 79:6651, which is incorporated herein by reference. For instance, the hybridomas may be created by fusing stimulated B cells, obtained from a human immunized with the primary (idiotype) antibody (Ab1) to which the anti-idiotype (Ab2) is to be made, with a mouse/human heterohybrid fusion partner. A variety of such fusion partners have been described. See, for example, James and Bell, J. Immunol. Meths. (1987) 100:5-04 and U.S. Pat. No. 4,624,921, which are incorporated herein by reference. A mouse/human fusion partner may be constructed by fusing human lymphocytes stimulated or transformed by EBV with readily available mouse myeloma lines such as NS-1 or P3NS-1, in the presence of polyethylene glycol, for instance. The hybrid should be suitably drug-marked, which may be accomplished by cultivation of the hybrid in increasing concentrations of the desired drug, such as 6-thioguanine, ouabain, or neomycin.

According to an alternative embodiment of the present invention, the immortalization of cells producing the human anti-idiotype antibodies of interest may be accomplished using EBV transformation techniques. For example, B-lymphocytes derived from peripheral blood, bone marrow, lymph nodes, tonsils, etc. of patients immunized with the idiotype antibody are immortalized using EBV according to methods such as those described in U.S. Pat. No. 4,464,465 and Chan et al., J. Immunol. (1986) 136:106, which are incorporated herein by reference.

The hybridomas or lymphoblastoid cells which secrete anti-idiotypic antibody of interest may be identified by screening culture supernatants against antibody which is specific for gp72, preferably the antibody to gp72 which was used to immunize the patient. Cells from wells possessing the desired activity are cloned and subcloned in accordance with conventional techniques and monitored until stable immortalized lines producing the human monoclonal antibody of interest are identified. The monoclonal antibodies thus produced may be of the IgG, IgM, IgA or IgD isotype, and may further be any of the subclasses of IgG, such as $IgG_1$, $IgG_2$, $IgG_3$, or $IgG_4$. By monoclonal antibody is meant an antibody produced by a clonal, continuous cell line separate from cells which produce monoclonal antibodies of a different specificity. Thus such antibodies are produced isolated from other antibodies and, accordingly, in substantially pure form at a concentration greater than normally occurring in human serum.

The cell lines of the present invention may also be fused with other cells to produce hybridomas or heterohybridomas, and thus provide for the transfer of genes encoding the human monoclonal antibodies. Alternatively, recombinant DNA techniques may be used to isolate and transfer the DNA encoding the immunoglobulins or regions thereof which include the idiotopes which are an internal image of a gp72 epitope to a variety of hosts for specific antibody production. See, for example, EP 173,494 and EP 239,400, which are incorporated herein by reference. Thus, an anti-idiotypic human monoclonal antibody of the present invention is intended to include idiotopic regions of the variable domains of human immunoglobulin molecules which elicit the desired immunogenic or therapeutic responses.

For instance, DNA encoding framework- or paratope-associated idiotopes or idiotypic regions of a human anti-idiotypic immunoglobulin molecule of interest may be cloned as part of the variable region, or separately once a particular region of interest has been identified and sequenced. The regions may be cloned into a vector for expression in a host. For example, constructs which code for the idiotopic region of interest and a vaccinia virus gene may be prepared, and a recombinant vaccinia virus may be used to immunize a patient to the idiotopic region which mimics a gp72 epitope or otherwise regulates the immune response to gp72-bearing tumors or prevents the formation of such tumors. See U.S. Pat. No. 4,722,848, which is incorporated herein by reference.

Using recombinant DNA techniques, "class-switching" may readily be accomplished whereby genes encoding the constant regions which determine the isotype of the immunoglobulin molecule of interest are exchanged or replaced by genes encoding a different isotype or different subclass of an isotype. Class-switched immunoglobulins may also be isolated by selecting cells which have undergone spontaneous switching using methods well known to those skilled in the art.

As an illustrative example of the present invention, antibody 105AD7 is produced by the mouse/human heterohybridoma described in Example 1, below. The 105AD7 human antibody is of the $IgG_1$ isotype and binds specifically to murine monoclonal antibody 791T/36. A hybridoma cell line producing the 791T/36 antibodies was deposited with the American Type Culture Collection, 10801 University Boulevard, Manassas, Va. 20110-2209 on Aug. 14, 1986 and was assigned accession number HB 9173. The 105AD7 antibody binds to 791T/36 in a manner such that the binding of 791T/36 to the gp72 is blocked, and thus may represent an internal image of an epitope of the gp72 antigen. By "blocked" is meant that in assays to measure the binding of 791T/36 to purified gp72 or cells bearing the gp72 antigen, preincubation of 791T/36 with 105AD7 significantly reduces the subsequent ability of 791T/36 to bind gp72.

A hybridoma cell line producing the 105AD7 antibodies has been deposited with the American Type Culture Collection, 10801 University Boulevard, Manassas, Va. 20110-2209 on Oct. 11, 1988 and has been assigned accession number HB 9857.

Included within the present invention are human monoclonal antibodies similar to 105AD7, including those of different isotypes, affinities and biological functions. While a specific example of an antibody of the invention, 105AD7, binds to idiotopes of a particular anti-gp72 murine monoclonal antibody, 791T/36, this is not meant to be a limitation. Human monoclonal antibodies which bind to other idiotypic sites on 791T/36 or other antibodies specific for gp72 are contemplated by this invention. Such antibodies may be readily produced and identified based on the teachings contained herein. Additionally, human anti-idiotypic monoclonal antibodies which represent the internal image of an epitope of the gp72 antigen may be used to produce other human anti-anti-idiotype monoclonal antibodies, which antibodies bind the gp72 antigen and may be useful therapeutically.

The human monoclonal antibodies of this invention may be used intact or as immunogenic fragments, such as $F_v$, Fab, or $F(ab')_2$ fragments, but usually intact. The fragments may be obtained from antibodies by conventional techniques, such as by proteolytic digestion of the antibody using pepsin or papain, or by recombinant DNA techniques in which DNA encoding the desired fragment is cloned and expressed in a variety of hosts.

The human anti-anti-gp72 monoclonal antibodies of this invention find particular utility in compositions containing an immunogenic or therapeutic amount of at least one of the monoclonal antibodies of this invention. An immunogenic or therapeutic amount is an amount which stimulates an immune response of a humoral and/or cellular nature in an immunized host, whereby the host's immune system exhibits increased activity against tumor cells bearing gp72 antigen. Thus the compositions have a therapeutic or protective effect in the afflicted host, in that the tumor cells are eliminated or partially arrested.

Adjuvants may be employed in the pharmaceutical compositions to facilitate stimulation of the host's immune response, and may include, but are not limited to, aluminum hydroxide, lysolecithin, pluronic polyols, polyanions, peptides, proteins and oil emulsions. The anti-idiotypic antibodies of the invention may also be coupled to immunogenic carriers or cross-linked. Physiologically-accepted carriers such as saline, sterile water, phosphate buffered saline, and the like, may also be used in the compositions. Other buffering and dispersing agents and inert non-toxic substances suitable for delivery to a patient may be incorporated in the pharmaceutical compositions and are well known to those skilled in the art. The solutions for administration are sterile and generally free of particulate matter. The compositions may be sterilized by conventional sterilization techniques. The concentration of antibody in the formulations can vary widely, i.e., from less than about 0.01%, usually at least 0.5%, to as much as 15 to 20% by weight and will be selected primarily based on fluid volumes, viscosities, antigenicity, etc., in accordance with the particular mode of administration selected.

The human monoclonal antibodies and pharmaceutical compositions of this invention are particularly suitable for parenteral administration, i.e., intravenously, intramuscularly, or subcutaneously. The compositions are administered to a patient diagnosed as having or suspected of having a tumor which bears the gp72 antigen, or may be administered prophylactically to a person predisposed to such disease. By "bearing gp72 antigen" is meant tumor cells which themselves express the gp72 antigen, or tumor cells to which the gp72 antigen has otherwise become bound or associated. The gp72 antigen is desirably accessible or may be made accessible to the antibodies or cells responding to the administration of the anti-idiotypic antibodies of the invention.

The compositions are administered in amounts sufficient to stimulate an immune response so that tumor cells are eliminated or partially inhibited. Amounts effective for this use will depend upon the severity of the disease and the status of the patient's immune system, but generally range from about [0.1 $\mu$g] to about [1 mg] of antibody per kilogram of body weight, with dosages of [1 $\mu$g] to [200 $\mu$g] per kilogram being more commonly used. Administration may be once or a plurality of times over a prolonged period. As the materials of this invention may be employed in serious disease states, that is, life-threatening or potentially life-threatening situations, substantial excesses of these human monoclonal antibodies may be administered if desired by the treating physician in view of the absence of extraneous substances and the absence of "foreign substance" rejection in a human host. Actual methods of preparing and administering pharmaceutical compositions, including preferred dilution techniques for injections of the present compositions, are well known or will be apparent to those skilled in the art and are described in more detail in, for example, *Remington's Pharmaceutical Science*, 16th Ed., Mack Publishing Co., Penn. (1982), which is incorporated herein by reference.

The human monoclonal antibodies may also be used in combination with other antibodies, which are preferably human, or may be given in conjunction with other chemotherapeutic agents. If the additional antibodies employed bind the gp72 antigen, they desirably do not bind the anti-idiotypic antibodies also administered. To achieve possible synergistic action between the components the additional antibodies may bind determinants of gp72 which are not recognized by the immune response engendered by the anti-idiotypic antibodies of the invention which are also administered. The additional monoclonal antibodies may be administered separately or in conjunction with the antibodies of this invention, which may themselves be conjugated to chemotherapeutic agents. For instance, U.S. Pat. Nos. 4,590,071 and 4,671,958, which are incorporated herein by reference, describe the coupling of ricin A chain to a monoclonal antibody for targeting to human tumor cells.

The effectiveness of the human monoclonal antibodies of the present invention may be monitored in vitro or in vivo. Desirably the anti-idiotypic antibodies will, upon administration to a patient, elicit and/or regulate an immune response against cells which carry the gp72 antigen. The immune response may be induced de novo, or previously primed cells may be selected and amplified. The antitumor reactivity may be of a humoral and/or cellular nature. Humoral responses may be monitored in vitro by conventional immunoassays, where the antitumor activity of the response may be determined by complement-mediated cellular cytotoxicity and antibody-dependent cellular cytotoxicity (ADCC) assays. The assay formats are well known to those skilled in the art and are described in, for example, *Handbook of Experimental Immunology*, Vol. 2, D. M. Weir, ed. 2d edition, Blackwell Scientific Publications, Oxford (1986), which is incorporated herein by reference. Other assays may be directed to the level of tumor antigen, such as gp72, in the patient or tissue. Cell-mediated immunity may be monitored in vivo by the development of delayed-type hypersensitivity reactions or other in vivo or in vitro means known to those skilled in the art.

The monoclonal antibodies of the invention can further find a wide variety of utilities in vitro. By way of example, the anti-idiotypic antibodies can be used to analyze immune responses to gp72 antigen of humans or animals, and may serve as functional substitutes for gp72. The monoclonal antibodies may be labeled by various means known to those skilled in the art, where label serves as a convenient means for determining the extent to which the anti-idiotype antibody is bound by idiotypic, anti-analyte antibody in an immuno-assay. Label can be a radioisotope, enzyme chromophore, fluorophore, light-absorbing or refracting particle, magnetic or colloidal particle, etc. It is also possible to indirectly label the anti-idiotype antibody with a labeled antibody directed against a non-idiotypic antigenic determinant on the anti-idiotype antibody, e.g., a directly labeled, heterologous antibody directed against a determinant in the Fc region of the anti-idiotype antibody. Immunoassays in which the anti-idiotype antibodies may be employed are numerous, such as, for example, U.S. Pat. Nos. 4,536,479, 3,654,090, 4,233,402 and 4,016,043, which are all incorporated herein by reference. Also, the anti-idiotypic anti-bodies may be used in vitro to stimulate cells removed from a host which are then returned to the host after clonal activation and/or selection.

The following examples are offered by way of illustration and not limitation.

EXPERIMENTAL

EXAMPLE 1

A. Obtaining Suitable Human B Cells

Human B lymphocytes suitable for fusion were obtained from the peripheral blood of an individual who three years previously had been given $^{131}$I-791T/36 for radiolocalization of a colorectal carcinoma. The patient gave a vigorous skin reaction to an intradermal challenge with mouse antibody, and fourteen days later peripheral blood was drawn and the lymphocytes separated by standard separation techniques. The cells were washed twice in Hanks balanced salt solution and resuspended in Dulbecco's Modified Eagle's Medium (DMEM) supplemented with 10% fetal calf serum (FCS) and counted using a hemocytometer. Approximately $2\times10^6$/ml lymphocytes were cultured in vitro in DMEM+10% FCS for four days, stimulated with adjuvant peptide (N-acetylmuramyl-L-alanyl-D-isoglutamine) at a concentration of 50 $\mu$g/ml, and with 1 $\mu$g/ml purified 791T/36 antibody.

B. Fusion of Stimulated B Cells with Mouse/Human Heterohybrid

Hybrid cells secreting human monoclonal antibodies to 791T/36 were created by fusing the stimulated B cells with a mouse/human heterohybrid fusion partner, EL41. The EL41 line was constructed by first fusing human lymphnode lymphocytes stimulated with Epstein-Barr virus with the mouse myeloma line P3NS1 in the presence of 50% polyethylene glycol (PEG). Six resultant hybrids were grown in the presence of increasing concentrations of 6-thioguanine, starting with 2 $\mu$g/ml and increasing biweekly in 2 $\mu$g/ml increments up to 10 $\mu$g/ml, then in 5 $\mu$g/ml increments. One hybrid was resistant to 6-thioguanine at a concentration of 30 $\mu$g/ml, and a secondary fusion between this line and unstimulated human lymphnode lymphocytes on 50% PEG was performed. One line, designated EL41, was isolated from the fusion which was stable in 30 $\mu$g/ml 6-thioguanine. This line produced human lambda light chain.

The stimulated human peripheral blood lymphocytes were suspended with EL41 cells at a ratio of 3:2, respectively, in 50% PEG for 1 minute at 22° C. according to the procedure of Galfre et al., *Nature* (1977) 266:555. The final hybrid cell suspension was diluted to a concentration of $2.25\times10^5$ cells/ml in DMEM containing 10% FCS and HMT ($1\times10^{-4}$ M hypoxanthine, $1\times10^{-5}$ M methotrexate, and $1.6\times10^{-5}$ M thymidine). The mixture was plated (200 $\mu$l/well) into two 96-well tissue culture plates containing rat peritoneal exudate cells (PEC) as feeder cells. Cultures were fed by removal and replacement of 50% of the volume of each well with fresh DMEM-FCS-HMT every two to three days. The wells were observed with an inverted microscope for signs of cell proliferation. Twenty-one days post plating, it was observed that 15 wells contained proliferating cells.

Supernatants from the wells with growth were removed and preliminarily screened for the presence of anti-791T/36 antibodies using the ELISA described below. Two wells were detected in which the hybrids secreted human antibody reactive with 791T/36 and not reactive with other murine $IgG_{2a}$ and $IgG_{2b}$ antibodies. However, one of these lines ceased antibody production after four weeks. The remaining line, designated 105AD7, was subjected to several rounds of cloning by limiting dilution in DMEM plus 10% FCS and HMT until all clonal supernatants assayed by the ELISA procedure gave a positive reaction in the 791T/36 antigen wells. The cloning procedure involved distributing the initial hybrid cells over six 96-well micro-culture plates containing rat PEC as a feeder layer. The supernatants from the resulting outgrowth were screened for activity against 791/T6, and cells from positive wells were cloned again at 2 cells/well. Wells containing single colonies were again screened for antibody production and then cloned again into 96-well micro-culture plates at 2 cells/well.

The cell line designated 105AD7 was deposited with the American Type Culture Collection (ATCC), Rockville, Md. on Oct. 11, 1988 and has Accession Number HB 9857.

C. Characterization of Human Monoclonal Antibody 105AD7

The reactivity of monoclonal antibody 105AD7 obtained from the 105AD7 hybridoma was assayed using an ELISA procedure. Wells of 96-well PVC microtiter plates (Titertek Immunoassay plate, Flow Laboratories) were coated with mouse monoclonal antibody (50 μl/well of a 5 μg/ml solution in PBS, resulting in 250 ng/well) and incubated overnight at 4° C. Plates were then washed in phosphate buffered saline (PBS)/0.05% TWEEN 20 (Sigma) and blocked with a solution of PBS/1% bovine serum albumin (BSA), 200 μl/well, and incubated 2 hours at room temperature. The blocking solution was removed by inverting the plates and "flicking". The culture supernatant from the well to be tested was added to duplicate wells, 25 μl/well, and incubated at room temperature for 30 minutes. The plates were then washed five times with PBS/0.05% Tween 20, and 50 μl goat anti-human IgG (γ-chain specific) or IgM (μ-chain specific)—alkaline phosphatase conjugate (1:1000 dilution in PBS/1% BSA) (Sigma) added to each well. Following an incubation period of 30 minutes at room temperature, the wells were again washed five times with PBS/0.05% Tween 20, then 150 μl substrate (p-nitrophenyl phosphate, disodium (Sigma), 1 mg/ml in 0.1 M glycine buffer, pH 10.4, containing 0.001 M $MgCl_2$ and 0.001 M $ZnCl_2$) was added to each well, the plates incubated for 30 minutes in the dark at 22° C. and the absorbance at 405 nm determined using a Titertek Multiskan reader (Flow Laboratories, Ltd.).

The human monoclonal antibody 105AD7 reacted specifically with murine monoclonal antibody 791T/36, as shown in Table 1. The 105AD7 antibody showed higher reactivity with the $IgG_{2b}$ form of 791T/36 than the $IgG_{2a}$ class switch variant of 791T/36 which had been previously obtained using clonal selection. The 105AD7 antibody did not show significant binding to a variety of murine monoclonal antibodies specific for antigens other than the gp72 antigen. The other antibodies included two of the $IgG_{2b}$ isotype, five of the $IgG_1$ isotype, two $IgG_{2a}$, $IgG_{2b}$ myeloma protein, and one IgM antibody.

TABLE 1

Reactivity of Human Monoclonal Antibody 105AD7 Against Different Mouse Monoclonal Antibodies Using ELISA

| Mouse Antibody No. | Target Antigen | Isotype | 105AD7 Anti-Human Ig Conjugate | Anti-mouse Ig Conjugate[a] |
|---|---|---|---|---|
| 791T/36[b] | gp72 | $IgG_{2b}$ | 1.202 | — |
| 791T/36[b] | gp72 | $IgG_{2a}$ | 0.513 | — |
| Myeloma | — | $IgG_{2b}$ | 0.151 | — |
| 533 | Methotrexate | $IgG_{2b}$ | 0.126 | 2.577 |
| 381 | — | $IgG_{2b}$ | 0.173 | 2.536 |
| C365 | CEA[c] | $IgG_1$ | 0.239 | 1.656 |
| C198 | CEA/NCA[d] | $IgG_1$ | 0.107 | 0.756 |
| C161 | CEA/NCA | IgG1 | 0.169 | 0.904 |
| B14B8 | CEA/NCA | $IgG_1$ | 0.158 | 0.699 |
| C24 | CEA/NCA | $IgG_1$ | 0.173 | 1.769 |
| C228 | CEA | $IgG_{2a}$ | 0.131 | 1.415 |
| C337 | CEA | $IgG_{2a}$ | 0.087 | 1.079 |
| Myeloma | — | $IgG_{2a}$ | 0.114 | — |
| B55 | EMA[e] | IgM | 0.096 | 1.959 |

[a]The anti-mouse conjugate was used to demonstrate binding of mouse antibody to the PVC plate.
[b]Class switch variant of 791T/36.
[c]Carcinoembryonic antigen.
[d]Normal Cross-Reacting Antigen.
[e]Epithelial Membrane Antigen.

D. Specificity Analysis of 105AD7

Anti-idiotypic antibodies in sera from patients receiving radiolabeled murine monoclonal antibody 791T/36 for imaging studies have been detected using a flow cytometry assay which measures the inhibition of binding of fluorescein isothiocyanate (FITC) labeled 791T/36 with target 791T sarcoma cells. Robins et al., *J. Immunol. Meths.* (1986) 90:165. Thus human monoclonal antibody 105AD7 was tested using this protocol for its ability to inhibit the binding of 791T/36 to its target antigen.

Murine monoclonal antibody 791T/36 was labeled with FITC using the procedure of Roe et al., *Mol. Immunol.* (1985) 22:11. The 791T/36-FITC conjugate, suspended in DMEM containing 2% FCS at 100 ng conjugate/100 μl medium, was then incubated at 4° C. for 30 minutes with different dilutions of human monoclonal antibody 105AD7 (200 μl of hybridoma culture supernatant or purified antibody in DMEM/2% FCS). Target 791T cells which express the gp72 antigen were added to the monoclonal antibody mixture at a concentration of $10^5$ cells/100 μl DMEM+2% FCS, and incubated an additional 30 minutes at 4° C. The binding of FITC-labeled mouse antibody 791T/36 to target 791T cells, as indicated by fluorescent intensity, was measured using a fluorescence-activated cell sorter, FACS IV.

The results of the FACS inhibition assay showed that human monoclonal antibody 105AD7 completely blocked the binding of 791T/36-FITC to target 791T cells. Complete inhibition of both the 791T/36 $IgG_{2b}$ and 791T/36 $IgG_{2a}$ class switch variant binding was obtained using 105AD7 culture supernatant dilutions of 1:1 and 1:5, while 50% inhibition of 791T/36-FITC (100 ng) was observed with approximately 40 ng of purified 105AD7. Results are shown in FIG. 1.

The specificity of inhibition of 105AD7 for 791T/36 was confirmed using an anti-CEA murine monoclonal antibody, 228 ($IgG_{2a}$). FITC-labeled 228 was preincubated with 105AD7 and the binding with a CEA target assessed by FACS. No inhibition of binding of 228 to its target CEA+ cells was observed.

The specificity of 105AD7-mediated inhibition of 791T/36 binding was further defined using gastric carcinoma MKN45 cells. These cells express both the CEA and gp72 antigens. 105AD7 effectively inhibited the binding of the IgG$_{2a}$ variant of 791T/36-FITC to MKN45 cells at dilutions of 1:1 and 1:5, but did not inhibit the binding of 228-FITC to the CEA antigen.

Thus human monoclonal antibody 105AD7 may represent the internal image of the gp72 antigen. The strong blocking activity of 105AD7 indicates that it binds either within or very close to the paratope of 791T/36.

EXAMPLE 2

Stimulation of Anti-Anti-Idiotypic Responses

Immunization of rats and rabbits with human monoclonal antibody 105AD7 has resulted in immune responses to 105AD7. Four Wistar rats were immunized intraperitoneally with 105AD7 in Freund's complete adjuvant (FCA), 115 μg, and were boosted with 115 μg in Freund's incomplete adjuvant two weeks later. Sera were drawn prior to immunization and at weeks 1, 2, 3 and 4 after the first injection, and assayed by ELISA and FACS inhibition. Four New Zealand white rabbits were also immunized intramuscularly with 105AD7 150 μg in FCA and monitored for immune responses.

Sera from the rats obtained prior to immunization with 105AD7 did not react in ELISA with either the 105AD7 antibody or sarcoma 791T cells bearing the gp72 antigen. ELISAs were performed essentially as described in Example 1, except that the 791T cells were fixed to the plates with 0.05% glutaraldehyde for 10 minutes at 22° C. Following immunization with 105AD7, however, sera at one through four weeks reacted with both the 105AD7 immunoglobulin and with 791T cells, as shown in Table 2.

FACS analysis involved an indirect binding assay to measure the anti-791T reactivity of sera from the immunized rats. Briefly, 100 μl of immune or control sera were incubated with 2×10$^5$ 791T cells or colon carcinoma C170 cells for 25 minutes at 4° C. (C170 cells also express the gp72 antigen). The cells were washed and then incubated with goat anti-rat IgG-FITC conjugate for 25 minutes at 4° C., washed, resuspended and then analyzed in the cell sorter. The results (Table 2) showed that rat anti-105AD7 sera bound both 791T and C170 cells while non-immune sera did not. Murine 791T/36 antibody strongly bound 791T cells and somewhat less to C170 cells.

TABLE 2

FACS Analysis of Anti-791T Reactivity of
Sera from Rats Immunized with 105AD7

| | Mean Linear Fluorescence/Cell | | | |
|---|---|---|---|---|
| | Sarcoina 791T | | Colon Carcinoma C170 | |
| Rat Serum Dilution | Non-immune[a] | Immune[b] | Non-immune[a] | immune[b] |
| 1/5 | 26 | 100 | 30 | 92 |
| 1/10 | 20 | 86 | 22 | 56 |
| 1/20 | 15 | 76 | 16 | 43 |
| 1/40 | 13 | 54 | 15 | 35 |
| 1/80 | 12 | 45 | 15 | 25 |
| 791T/36 | 2693 | | 241.6 | |

[a]Pre-immunization
[b]Four weeks post-immunization

EXAMPLE 3

Characterization of Anti-Tumor Cell Activity Induced by Immunization with 105AD7

Humoral immune responses induced by 105AD7 may mediate activity against a tumor bearing the gp72 antigen by activating complement- or antibody-dependent cellular cytotoxicity (CDCC or ADCC). For instance, the antibodies produced following 105AD7 immunization which fix complement may eliminate tumor cells expressing the gp72 antigen via complement-mediated membrane damage or increased susceptibility to phagocytosis.

ADCC is characterized by selective killing of gp72-bearing cells in which "non-immune" lymphocytes are a source of effector cells. A $^{51}$Cr-release test is used to detect ADCC of target tumor cells, such as that described by Braggemann et al., *J. Exp. Med.* (1987) 106:1351, which is incorporated by reference herein. Briefly, peripheral blood lymphocytes are obtained from healthy animals or patients which have not been immunized with monoclonal antibody 105AD7 (as well as from immunized animals or patients as controls), to provide effector cells. Target cells bearing the gp72 antigen, such as 791T sarcoma cells, are labeled by incubation with $^{51}$Cr for 1 hour at 37° C., after which they are washed and resuspended in medium. The labeled cells are seeded 2×10$^4$ cells/well, in microculture plates. Immune sera from animals or patients immunized with 105AD7 is then added to the wells, followed by 6×10$^5$ lymphocytes/well. The mixtures are incubated for 4 hours, after which the plates are briefly centrifuged and the radio-activity in samples of the supernatants is counted and percent cytotoxicity is thereby determined.

The $^{51}$Cr-release assay may also be used to test the ability of antibodies in sera of animals or patients immunized with 105AD7 to kill gp72-bearing cells in the presence of non-immune serum as a source of complement (CDCC). It is carried out similarly to the assays for ADCC except that undiluted, unheated serum is added to the microtest well instead of a suspension of effector cells.

The induction of cell-mediated immunity in response to immunization with a human anti-idiotypic antibody to the gp72 antigen may be important in the rejection of tumors bearing the gp72 antigen and is also monitored. The procedure of Lee et al., *Proc. Natl. Acad. Sci. USA* (1985) 82:6286, which is incorporated herein by reference, may be used. Briefly, animals or patients which have been immunized with human anti-idiotypic antibodies to the gp72 antigen, such as 105AD7, are subsequently challenged with an inoculum of active or, in the case of humans, inactivated tumor cells bearing the gp72 antigen, such as 791T cells. The challenge inoculum is given as a footpad or other intradermal injection, and delayed type hypersensitivity (DTH), as a measure of CMI, is determined by measuring the swelling of the footpad or skin. The leukocyte adherence inhibition test, described in Lee et al., supra, may be used as an in vitro correlate of the DTH assay.

From the foregoing, it will be appreciated that the cell line of the present invention provides compositions of human anti-idiotypic monoclonal antibodies which are capable of generating an immune response to the gp72 antigen associated with a variety of tumors. This allows therapeutic and prophylactic compositions to tumors bearing such antigen to be more easily developed. In addition, the cell line provides antibodies which find use in in vitro applications, imaging and other well known procedures.

Although the present invention has been described in some detail by way of illustration and example for purposes of clarity and understanding, it will be obvious that certain changes and modifications may be practiced within the scope of the appended claims.

What is claimed is:

1. The human monoclonal antibody, Fv, or Fab or F(ab')$_2$ fragment thereof, produced by hybridoma cell line 105AD7 having ATCC Accession No. HB 9857.

2. The human monoclonal antibody, or Fv, Fab of F(ab')$_2$ immunogenic fragment thereof, produced by hybridoma cell line 105AD7 having ATCC Accession No. HB 9857.

3. A cell line that produces the human monoclonal antibody, according to claim 2.

4. A composition useful in treating patients with tumors that bear a gp-72 tumor-associated antigen, the composition comprising a therapeutic amount of the human monoclonal antibody, or immunogenic fragment thereof, according to claim 2 and a pharmaceutically acceptable carrier.

5. A method for treating patients with colorectal tumors that bear a gp-72 tumor-associated antigen, the method comprising administering to the patients a therapeutic amount of the human monoclonal antibody, or immunogenic fragment thereof, according to claim 2.

* * * * *